United States Patent
Wakabayashi et al.

(10) Patent No.: US 12,370,224 B2
(45) Date of Patent: Jul. 29, 2025

(54) COMPOSITION CONTAINING PROPIONIBACTERIUM FREUDENREICHII AND USES THEREOF

(71) Applicant: MEIJI CO., LTD., Tokyo (JP)

(72) Inventors: Jun Wakabayashi, Tokyo (JP); Katsunori Kimura, Tokyo (JP)

(73) Assignee: MEIJI CO., LTD., Tokyo (JP)

( * ) Notice: Subject to any disclaimer, the term of this patent is extended or adjusted under 35 U.S.C. 154(b) by 713 days.

(21) Appl. No.: 17/625,864

(22) PCT Filed: Jul. 17, 2020

(86) PCT No.: PCT/JP2020/027761
§ 371 (c)(1),
(2) Date: May 13, 2022

(87) PCT Pub. No.: WO2021/015107
PCT Pub. Date: Jan. 28, 2021

(65) Prior Publication Data
US 2023/0044923 A1    Feb. 9, 2023

(30) Foreign Application Priority Data
Jul. 19, 2019  (JP) .................. 2019-133853

(51) Int. Cl.
A61K 35/74     (2015.01)
A23L 33/135    (2016.01)
A61K 31/702    (2006.01)
A61P 3/04      (2006.01)

(52) U.S. Cl.
CPC ............ *A61K 35/74* (2013.01); *A23L 33/135* (2016.08); *A61K 31/702* (2013.01); *A61P 3/04* (2018.01); *A23V 2200/332* (2013.01); *A23V 2400/617* (2023.08)

(58) Field of Classification Search
CPC .... A61K 35/74; A61K 33/702; A61K 33/701; A23L 33/135; A23L 33/701
See application file for complete search history.

(56) References Cited

U.S. PATENT DOCUMENTS

| | | | |
|---|---|---|---|
| 9,095,159 B2* | 8/2015 | Sera | A61P 1/04 |
| 2011/0020389 A1 | 1/2011 | Kunieda et al. | |
| 2012/0134973 A1* | 5/2012 | Kekkonen | A61K 35/747 |
| | | | 424/93.51 |
| 2012/0276055 A1 | 11/2012 | Sera et al. | |
| 2015/0359238 A1 | 12/2015 | Suzuki et al. | |
| 2018/0160712 A1 | 6/2018 | O'Hara et al. | |

FOREIGN PATENT DOCUMENTS

| | | |
|---|---|---|
| CN | 104413334 | 3/2015 |
| CN | 107412422 | 12/2017 |
| CN | 109152728 | 1/2019 |
| JP | 59-82313 | 5/1984 |
| JP | 2000-256201 | 9/2000 |
| JP | 2003-504409 | 2/2003 |
| JP | 2011-516402 | 5/2011 |
| JP | 2012-201599 | 10/2012 |
| JP | 2014-166160 | 9/2014 |
| JP | 2018-515576 | 6/2018 |
| WO | 01/05413 | 1/2001 |
| WO | 2009/069498 | 6/2009 |
| WO | 2011/071134 | 6/2011 |
| WO | 2011/078213 | 6/2011 |
| WO | 2014/163031 | 10/2014 |

OTHER PUBLICATIONS

Vorobjeva, L. I., Khodjaev, E. Yu., & Vorobjeva, N. V. (2008). Propionic acid bacteria as probiotics. Microbial Ecology in Health and Disease, 20(2), 109-112. https://doi.org/10.1080/08910600801994954 (Year: 2008).*

Chinese Office Action issued Aug. 2, 2024 in corresponding Chinese Patent Application No. 202080044295.6, with English machine translation.

International Search Report (ISR) issued Sep. 29, 2020 in International (PCT) Application No. PCT/JP2020/027761.

Ikuo Kimura, "5. Obesity and the gut microbiota", Experimental Medicine, vol. 32, No. 5 (special issue), 2014, with machine translation, cited in the specification.

Junki Miyamoto et al., "I. A comprehensive study of intestinal bacteria and their metabolites 3. Intestinal bacteria and short-chain fatty acids", The Lipid, vol. 27, No. 2, Apr. 2016, with machine translation, cited in the specification.

Andrew J. Brown et al., "The Orphan G Protein-coupled Receptors GPR41 and GPR43 Are Activated by Propionate and Other Short Chain Carboxylic Acids", The American Society for Biochemistry and Molecular Biology, vol. 278, No. 13, pp. 11312-11319, 2003, cited in the specification.

T. Polyviou et al., "Randomised clinical study: inulin short-chain fatty acid esters for targeted delivery of short-chain fatty acids to the human colon", Alimentary Pharmacology and Therapeutics, 44, pp. 662-672, 2016, cited in the specification.

Nazarii Kobyliak et al., "Effect of alive probiotic on insulin resistance in type 2 diabetes patients: Randomized clinical trial", Diabetes & Metabolic Syndrome: Clinical Research & Reviews, vol. 12, pp. 617-624, 2018, cited in ISR.

Anna Oksaharju et al., "Effects of probiotic Lactobacillus rhamnosus GG and *Propionibacterium freudenreichii* ssp. shermanii JS supplementation on intestinal and systemic markers of inflammation in Apoe*3Leiden mice consuming a high-fat diet", British Journal of Nutrition, vol. 110, pp. 77-85, 2013, cited in ISR.

Tsuneyuki Oku, "Metabolism of New Sweetner Fructooligosaccharide (Neosugar®) and its Application", The Japanese Journal of nutrition and dietetics, vol. 44, No. 6, pp. 291-306, 1986, together with translation, cited in ISR.

(Continued)

*Primary Examiner* — Ruth A Davis
(74) *Attorney, Agent, or Firm* — Wenderoth, Lind & Ponack, L.L.P.

(57) ABSTRACT

There is provided a composition that comprises a propionic acid bacterium or a composition that comprises an oligosaccharide. The composition that comprises a propionic acid bacterium or the composition that comprises an oligosaccharide can suppress an increase of body weight of a subject by having the subject ingest the composition.

12 Claims, 2 Drawing Sheets

(56) References Cited

OTHER PUBLICATIONS

Evelyne Delmee et al., "Relation between colonic proglucagon expression and metabolic response to oligofructose in high fat diet-fed mice", Life Sciences, vol. 79, pp. 1007-1013, 2006, cited in ISR.
Office Action issued Jun. 13, 2023 in corresponding Japanese Patent Application No. 2019-133853, with English translation, 23 pages.
International Preliminary Report on Patentability and Written Opinion of the International Searching Authority issued Jan. 25, 2022 in International (PCT) Application No. PCT/JP2020/027761.
Office Action issued Jul. 15, 2023 in corresponding Chinese Patent Application No. 202080044295.6, with English translation, 18 pages.
Office Action issued Oct. 18, 2024 in Japanese Patent Application No. 2023-204937, with English-language translation.
Office Action issued May 27, 2025 in Japanese Patent Application No. 2023-204937, with English-language translation.

* cited by examiner

COMPOSITION CONTAINING PROPIONIBACTERIUM FREUDENREICHII AND USES THEREOF

CROSS-REFERENCE TO RELATED APPLICATION

The present patent application claims priority based on Japanese Patent Application No. 2019-133853, which is a Japanese application filed on Jul. 19, 2019, and the whole disclosures of this Japanese application are incorporated herein by reference as a part of this description.

BACKGROUND OF THE INVENTION

Field of the Invention

The present invention relates to a composition including a propionic acid bacterium or an oligosaccharide.

Background Art

In recent years, many people in developed countries including Japan, suffer from obesity and diabetes as a result of excessive energy intake due to excessive meals and high-calorie diets, which has become a major social problem. It has been revealed that intestinal flora is involved in energy control, nutrient absorption and the like of hosts and affects pathological conditions such as obesity and diabetes (see Non-Patent Document 1). Short chain fatty acid (SCFA), which is major metabolites of intestinal bacteria, not only provides energy for hosts, but also contributes to control of energy metabolism of hosts via receptors expressed in intestinal epithelial cells. The SCFA acts on the SCFA receptors GPR41 and GPR43, which are expressed mainly in the colon, to exacerbate production of the appetite-suppressing hormone PYY (peptide YY) and GLP-1 (glucagon-like peptide 1) which improves insulin sensitivity. In addition, they also have a function of increasing energy consumption of hosts and a function of suppressing hypertrophy of fat cells (see Non-Patent Document 2). Among the SCFA that acts, propionic acid is known to act on both GPR41 and GPR43 (see Non-Patent Document 3).

However, when propionic acid is taken orally, most of it is absorbed in the small intestine (see Non-Patent Document 4). Therefore, it is difficult for propionic acid to act on the receptors expressed in epithelial cells of the colon. Furthermore, probiotics, prebiotics, synbiotics or the like, which have the effect for producing a large amount of propionic acid, for example, in the colon, have not been revealed so far.

PRIOR ART DOCUMENTS

Non-Patent Documents

[Non-Patent Document 1] Ikuo Kimura, *Experimental Medicine*, Vol. 32, No. 5 (special issue), 2014
[Non-Patent Document 2] Junki Miyamoto et al., *The Lipid*, Vol. 27, No. 2, 2016-4
[Non-Patent Document 3] Andrew J. Brown et al., *The American society for biochemistry and molecular biology*, Vol. 278, No. 13, pp. 11312-11319, 2003
[Non-Patent Document 4] T. Polyviou et al, *Aliment Pharmacol Ther* 2016; 44:662-672

SUMMARY OF THE INVENTION

The present inventors have found that weight gain can be suppressed by having a subject ingest a composition including a propionic acid bacterium or an oligosaccharide. The present invention is based on these findings.

Thus, the present invention discloses a composition including a propionic acid bacterium or an oligosaccharide. The present invention provides the following inventions.

(1) A composition including a propionic acid bacterium.
(2) The composition according to (1), further including an oligosaccharide.
(3) The composition according to (2), wherein the oligosaccharide is a fructo-oligosaccharide.
(4) The composition according to any one of (1) to (3), wherein the propionic acid bacterium is *Propionibacterium freudenreichii*.
(5) The composition according to any one of (1) to (3), wherein the propionic acid bacterium is *Propionibacterium freudenreichii* ET-3.
(6) The composition according to any one of (1) to (5), which is a food composition or a pharmaceutical composition.
(7) The composition according to any one of (1) to (6), which is used for anti-obesity.
(8) The composition according to any one of (1) to (6), which is used for promoting propionic acid production.
(9) The composition according to any one of (1) to (6), which is used for promoting propionic acid production in the intestine.
(10) A method for preventing and/or treating obesity, including having a subject ingest an effective amount of the composition according to any one of (1) to (6).
(11) A method for promoting propionic acid production, including having a subject ingest an effective amount of the composition according to any one of (1) to (6).
(12) A method for promoting propionic acid production in the intestine, including having a subject ingest an effective amount of the composition according to any one of (1) to (6).
(13) A composition including an oligosaccharide.
(14) The composition according to (13), wherein the oligosaccharide is a fructo-oligosaccharide.
(15) The composition according to (13) or (14), which is a food composition or a pharmaceutical composition.
(16) The composition according to any one of (13) to (15), which is used for anti-obesity.
(17) The composition according to any one of (13) to (15), which is used for promoting propionic acid production.
(18) The composition according to any one of (13) to (15), which is used for promoting propionic acid production in the intestine.
(19) A method for preventing and/or treating obesity, including having a subject ingest an effective amount of the composition according to any one of (13) to (15).
(20) A method for promoting propionic acid production, including having a subject ingest an effective amount of the composition according to any one of (13) to (15).
(21) A method for promoting propionic acid production in the intestine, including having a subject ingest an effective amount of the composition according to any one of (13) to (15).
(22) A composition for anti-obesity including an oligosaccharide.
(23) A composition for promoting propionic acid production, including an oligosaccharide.
(24) A composition for promoting propionic acid production in the intestine, including an oligosaccharide.
(25) The composition according to any one of (22) to (24), wherein the oligosaccharide is a fructo-oligosaccharide.

(26) The composition according to any one of (22) to (25), which is a food composition or a pharmaceutical composition.

The present invention is advantageous in that weight gain can be suppressed by having a subject ingest the composition of the present invention.

DETAILED DESCRIPTION OF THE INVENTION

Deposit of Microorganism

Figure 1:
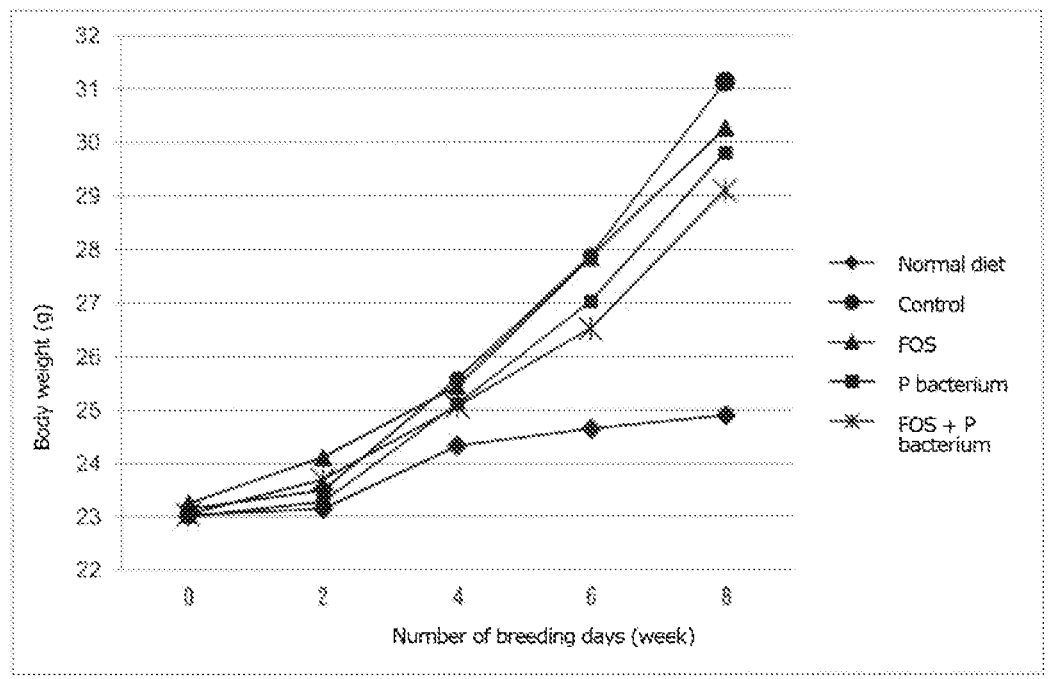
FIG. 1 shows the transitions in body weight (g) of mice over time (number of breeding days (weeks)) when normal diet, control, fructo-oligosaccharide (FOS), propionic acid bacterium (P bacterium), and FOS and propionic acid bacterium (FOS+P bacterium) were each fed to mice.

*Propionibacterium freudenreichii* ET-3 was deposited with the National Institute of Advanced Industrial Science and Technology Patent Microorganisms Depositary (Central 6, 1-1-1 Higashi, Tsukuba, Ibaraki, Japan) on Aug. 9, 2001, and then transferred to International Deposit and given Accession No. FERM BP-8115. Since the National Institute of Technology and Evaluation (IPOD, NITE) has taken over the patent microorganism deposit business from the National Institute of Advanced Industrial Science and Technology Patent Microorganisms Depositary (IPOD, AIST), as set forth in Budapest Notification No. 282 (http://www.wipo.int/treaties/en/notifications/budapest/treaty_budapest_282.html), *Propionibacterium freudenreichii* ET-3 is currently deposited with the National Institute of Technology and Evaluation (IPOD, NITE) (2-5-8-120 Kazusa-Kamatari, Kisarazu, Chiba) under Accession No. FERM BP-8115.

According to one aspect of the present invention, the composition of the present invention includes a propionic acid bacterium. The propionic acid bacterium used in the composition of the present invention may be living cells or dead cells, but is preferably living cells. The propionic acid bacterium that can be used in the present invention includes, but is not particularly limited to, those belonging to the genus *Propionibacterium*, the genus *Acidipropionibacterium*, the genus *Propionicimonas*, the genus *Propioniferax*, the genus *Propionimicrobium*, the genus *Propionivibrio* and the like, and is preferably a bacterium belonging to the genus *Propionibacterium*. Examples of bacterium belonging to the genus *Propionibacterium* include propionic acid bacterium such as *Propionibacterium freudenreichii*, *Propionibacterium thoenii*, *Propionibacterium jensenii*, *Propionibacterium avidum*, *Propionibacterium acnes*, *Propionibacterium lymphophilum*, and *Propionibacterium granulosam*. Among these propionic acid bacterium, *Propionibacterium freudenreichii* is more preferred, *Propionibacterium freudenreichii* IFO12424, *Propionibacterium freudenreichii* ATCC6207, and *Propionibacterium freudenreichii* ET-3 (FERM BP-8115) are more preferred, and *Propionibacterium freudenreichii* ET-3 (FERM BP-8115) is particularly preferred.

The number of propionic acid bacterium contained in the composition of the present invention is not particularly limited, but is preferably $1\times10^6$ to $1\times10^{12}$ cfu/mL, more preferably $1\times10^7$ to $1\times10^{11}$ cfu/mL, further preferably $1\times10^8$ to $1\times10^{10}$ cfu/mL, particularly preferably $5\times10^8$ to $5\times10^9$ cfu/mL. When the number of propionic acid bacterium contained in the composition of the present invention is set to $5\times10^8$ to $5\times10^9$ cfu/mL, weight gain can be more suppressed.

According to one preferred aspect of the present invention, the composition of the present invention can further include an oligosaccharide in addition to the propionic acid bacterium. The oligosaccharide is not particularly limited to those which about 2 to 10 monosaccharides, such as glucose and fructose, bind together. The oligosaccharide used in the composition of the present invention is preferably fructo-oligosaccharide, galacto-oligosaccharide, isomalto-oligosaccharide, xylo-oligosaccharide, genti-oligosaccharide, lactosucrose, fucosyllactose, nigero-oligosaccharide or the like, more preferably fructo-oligosaccharide. One or more of these oligosaccharides may be used. The fructo-oligosaccharide is a mixture of saccharides in which 1 to 3 molecules of fructose are bound to the fructose residue of sucrose. Example thereof includes 1-kestose, and, as a commercially available product, Meioligo (trademark) P manufactured by Meiji Food Materia Co., Ltd. may be used. Further, the propionic acid bacterium and the oligosaccharide provide the effect of the present invention even when they are not contained in the same composition, and thus may be administered to the subject separately. Therefore, it may be an aspect such as a kit including a composition comprising a propionic acid bacterium and a composition comprising an oligosaccharide.

When the composition of the present invention includes an oligosaccharide, the content of the oligosaccharide in the composition of the present invention is not particularly limited, but is preferably 2 to 8% by mass, more preferably 3 to 7% by mass, further preferably 4 to 6% by mass.

Propionic acid bacterium has an excellent weight gain suppressing effect, and thus can be provided by incorporating in foods which are taken daily or foods which are taken as supplements. That is, according to a preferred aspect of the present invention, a food composition including a propionic acid bacterium is provided. This food composition can be produced according to usual production procedures for the food, except that a propionic acid bacterium is incorporated in the food composition. Here, the food in which the propionic acid bacterium is incorporated may be in any form as long as it is a food which can contain a propionic acid bacterium. The form of the food is not particularly limited, as long as it is an orally-ingestible form, such as a solution, a suspension, an emulsion, a powder, a paste, a semi-solid forming product, or a solid forming product. Examples of the food include instant foods such as instant noodles, retort foods, canned foods, microwave foods, instant soups/miso soups, and freeze-dried foods; beverages such as soft drinks, fruit juice beverages, vegetable beverages, soy milk beverages, coffee beverages, tea beverages, powder beverages, concentrated beverages, and alcoholic drinks; wheat flour products such as bread, pasta, noodles, cake mix, and bread flour; confectioneries such as candy, caramel, chewing gum, chocolate, cookies, biscuits, bars, cakes, pies, snacks, crackers, Japanese confectioneries, mousse, and desserts; seasonings such as sauces, tomatoes processed seasonings, flavor seasonings, cooking mixes, sauces for dipping, dressings, seasoning soy sauces, and curry/stew ingredients; oils and fats such as processed fats, butter, margarine, and mayonnaise; dairy products such as dairy beverages, lactic beverages, fermented milk, cheeses, yogurts, lactic acid bacteria beverages, lactic drinks, cheeses, ice creams, creams, modified milk powder, liquid milk, and solid milk; processed agricultural products such as canned agricultural products, jams/marmalades, and cereals; frozen foods, and liquid foods.

When the propionic acid bacterium is incorporated in the food composition of the present invention, the food composition can be prepared by incorporating the propionic acid bacterium as it is in a food. The food composition is a food containing an effective amount of the propionic acid bacterium. Here, the phrase "containing an effective amount" of the propionic acid bacterium refers to a content of the propionic acid bacterium to be taken within a predetermined range, when a normally-eaten amount of an individual food is taken. It should be noted that an aspect in which a food composition is prepared by adding a propionic acid bacterium itself or a composition including the propionic acid bacterium to a food (for example, a beverage or yogurt), by a subject who takes it, also falls within the scope of the present invention.

According to the other preferred aspect of the present invention, a pharmaceutical composition including a propionic acid bacterium is provided. Here, the pharmaceutical composition is prepared as an oral formulation or a parenteral formulation according to a routine procedure in combination with additives that may be acceptable for drug formulation. When the pharmaceutical composition is an oral formulation, it can be in the form of a solid formulation such as a tablet, a powder, a fine granule, a granule, a capsule, a pill or a sustained-release tablet, or a liquid formulation such as a solution, a suspension or an emulsion. When the pharmaceutical composition is a parenteral formulation, it can be in the form of an injection or a suppository. From the viewpoint of easy ingestion (administration) to patients, the pharmaceutical composition is preferably an oral formulation. Here, examples of additives that may be acceptable for drug formulation include excipients, stabilizers, preservatives, wetting agents, emulsifiers, lubricants, sweeteners, colorants, flavors, buffers, antioxidants, and pH adjusters. The pharmaceutical composition of the present invention can be used in prevention and treatment of diseases due to weight gain and diseases due to a decrease in propionic acid concentration in the intestine, and, for example, can be used in prevention and/or treatment of obesity, diabetes, hyperlipemia or hypercholesterolemia.

When the composition including a propionic acid bacterium of the present invention is provided as a composition including one intake amount of the propionic acid bacterium, the composition is desirably provided in a unit packaging form so as to allow intake of one effective intake amount. When the composition is provided in a packaging form, it is desirable that a statement about the intake amount should be written on the packaging so as to allow intake of one effective intake amount, or that a document with the statement should be provided together. In addition, when the composition including a propionic acid bacterium of the present invention is continuously taken, this can have a more body weight suppressing effect and the like. For example, when a daily effective intake amount of the composition is provided in multiple packages, it may be provided as a set of the multiple packages containing the daily effective intake amount, for convenience of ingestion.

The packaging form for providing the composition including a propionic acid bacterium of the present invention is not particularly limited as long as it prescribes a fixed amount, and examples thereof include wrapping papers, wrapping sheets, bags, soft bags, paper containers, cans, bottles, capsules, containable containers such as plastic cases, and the like.

The person who takes the composition including a propionic acid bacterium of the present invention, himself/herself, can determine and take the intake amount thereof according to his/her bodily sensation. Therefore, the composition including a propionic acid bacterium of the present invention can preferably be provided in a form which enables adjustment of the intake amount according to the preference of the person who takes the composition, that is, in a form suitable for multiple intake. Examples of such forms include tablets, powders, gums, gummies and candies. Examples of the packaging form suitable for multiple intake include plastic cases, cans, bottles and wrapping papers.

The composition including a propionic acid bacterium of the present invention is preferably taken continuously for 3 days or more, more preferably taken for 1 week or more to provide the effect thereof better, and the administration and intake period thereof is more preferably 1 to 10 weeks, particularly preferably 2 to 9 weeks, further preferably 4 to 8 weeks. Here, the term "continuously" means that intake of a determined amount is continued every day. When the composition including a propionic acid bacterium of the present invention is provided in a packaging form, packages containing an effective intake amount for a certain period (for example, 1 week) may be provided as a set, for continuous intake.

According to a preferred aspect of the present invention, a composition for anti-obesity including a propionic acid bacterium is provided. Here, the term "anti-obesity" means that weight gain is suppressed, that the body weight reduces, or the like. The composition for anti-obesity of the present invention may be an anti-obesity agent, and this anti-obesity agent may be composed of a propionic acid bacterium.

According to a preferred aspect of the present invention, a composition for promoting propionic acid production including a propionic acid bacterium is provided. According to a more preferred aspect of the present invention, a composition for promoting propionic acid production in the intestine (preferably, in the colon) including a propionic acid bacterium is provided. The fact that the propionic acid production is promoted may be confirmed, for example, by directly measuring the propionic acid concentration in the intestine, but the level of the propionic acid concentration in the intestine can be indirectly measured by measuring the propionic acid concentration in feces.

According to a preferred aspect of the present invention, there is provided a method for preventing and/or treating obesity, including having a subject ingest an effective amount of the composition including a propionic acid bacterium of the present invention. Here, the subject may be an animal other than humans (a livestock such as a horse or a cow, a pet such as a dog or a cat, an animal for appreciation which is bred in a zoo, or the like), but is preferably a human. In addition, the subject that an effective amount of the composition including a propionic acid bacterium of the present invention is taken is preferably a subject who needs to suppress weight gain or a subject who needs to reduce the body weight. Also, according to the other preferred aspect of the present invention, there is provided a method for preventing and/or treating obesity (provided that medical actions to humans are excluded), including having a subject ingest an effective amount of the composition including a propionic acid bacterium of the present invention. The medical action means, for example, an action of taking (administering) a pharmaceutical product into a human, in need of a prescription of a doctor or the like.

According to a preferred aspect of the present invention, there is provided a method for promoting propionic acid production, including having a subject ingest an effective amount of the composition including a propionic acid bacterium of the present invention. According to a more preferred aspect of the present invention, there is provided a method for promoting propionic acid production in the intestine, including having a subject ingest an effective amount of the composition including a propionic acid bacterium of the present invention. According to the other preferred aspect of the present invention, there is provided a method for promoting propionic acid production (provided that medical actions to humans are excluded), including having a subject ingest an effective amount of the composition including a propionic acid bacterium of the present invention. According to the other more preferred aspect of the present invention, there is provided a method for promoting propionic acid production in the intestine (provided that medical actions to humans are excluded), including having a subject ingest an effective amount of the composition including a propionic acid bacterium of the present invention. Here, the phrase "medical actions to humans" is used in the same meaning as described above.

According to the other aspect of the present invention, a composition including an oligosaccharide (preferably, fructo-oligosaccharide) is provided. Here, the oligosaccharide and the like in the composition including an oligosaccharide of the present invention may be the same as the above-described oligosaccharide and the like which may be contained in the composition including a propionic acid bacterium of the present invention. Also, according to a preferred aspect of the present invention, a food composition or a pharmaceutical composition including an oligosaccharide (preferably, fructo-oligosaccharide) is provided. Here, the food composition or pharmaceutical composition including an oligosaccharide (preferably, fructo-oligosaccharide) of the present invention may be the same as the above-described food composition or pharmaceutical composition including a propionic acid bacterium of the present invention, and the unit packaging form and the like may be the same.

According to a preferred aspect of the present invention, a composition for anti-obesity including an oligosaccharide is provided. According to the other preferred aspect of the present invention, a composition for promoting propionic acid production (preferably, for promoting propionic acid production in the intestine) including an oligosaccharide is provided.

According to the other aspect of the present invention, there is provided a method for preventing and/or treating obesity, including having a subject ingest an effective amount of the composition including an oligosaccharide of the present invention. Here, the subject may be the same as that described above. Also, the effective amount of the composition including an oligosaccharide of the present invention and the like may be the same as the effective amount of the composition including a propionic acid bacterium of the present invention.

According to the other aspect of the present invention, there is provided a method for promoting propionic acid production (preferably, a method for promoting propionic acid production in the intestine), including having a subject ingest an effective amount of the composition including an oligosaccharide of the present invention.

According to the other aspect of the present invention, there is provided use of the composition of the present invention for preventing and/or treating obesity.

According to the other aspect of the present invention, there is provided use of the composition of the present invention for promoting propionic acid production. According to the other preferred aspect of the present invention, there is provided use of the composition of the present invention for promoting propionic acid production in the intestine.

According to the other aspect of the present invention, there is provided use of a propionic acid bacterium for manufacturing a composition for anti-obesity. The propionic acid bacterium can be used by washing a bacterial solution (living cells) activated and cultured in a medium for anaerobic bacteria with physiological saline, and then adjusting the number of bacteria to $5 \times 10^8$ to $5 \times 10^9$ cfu/mL.

According to the other aspect of the present invention, there is provided use of an oligosaccharide for manufacturing a composition for anti-obesity. The oligosaccharide can be prepared by containing the amount of 4 to 6% by mass in a composition (for example, a high fat diet), and used.

According to the other aspect of the present invention, there is provided use of a propionic acid bacterium and an oligosaccharide for manufacturing a composition for anti-obesity.

According to the other aspect of the present invention, there is provided use of a propionic acid bacterium for manufacturing a composition for promoting propionic acid production. According to the other preferred aspect of the present invention, there is provided use of a propionic acid bacterium for manufacturing a composition for promoting propionic acid production in the intestine.

According to the other aspect of the present invention, there is provided use of an oligosaccharide for manufacturing a composition for promoting propionic acid production. According to the other preferred aspect of the present invention, there is provided use of an oligosaccharide for manufacturing a composition for promoting propionic acid production in the intestine.

According to the other aspect of the present invention, there is provided use of a propionic acid bacterium and an oligosaccharide for manufacturing a composition for promoting propionic acid production. According to the other preferred aspect of the present invention, there is provided use of a propionic acid bacterium and an oligosaccharide for manufacturing a composition for promoting propionic acid production of in the intestine.

The propionic acid bacterium, oligosaccharide and the like used in the method for treating and/or preventing obesity of the present invention may be the same as the above-described propionic acid bacterium, oligosaccharide and the like contained in the composition of the present invention.

EXAMPLES

Hereinafter, the present invention will be described in detail based on the following examples, but is not limited to these examples.

Example 1: Confirmation of Weight Gain Suppressing Effect of Propionic Acid Bacterium (1) Test Method Male, 8-week-old C57BL/6J mice were divided into 5 groups and fed with a normal diet (AIN-93M) (manufactured by Oriental Yeast Co., Ltd.) or a high fat diet (HFD-60) (manufactured by Oriental Yeast Co., Ltd.). The groups fed with a high fat diet were administered with fructo-oligosaccharide (hereinafter, also referred to as "FOS"), a propionic acid bacterium (*Propionibacterium freudenreichii* ET-3, Accession No. FERM BP-8115, hereinafter also referred to as "P bacterium"), or both FOS and a propionic acid bacterium (hereinafter, also referred to as "FOS+P bacterium"), and bred for 8 weeks. The group fed with the high fat diet, but not administered with FOS and a propionic acid bacterium was defined as a control group. Meioligo (trademark) P (manufactured by Meiji Food Materia Co., Ltd.) was used as FOS, which was incorporated in the high fat diet in an amount of 5% by mass, and administered. A bacterial solution (living cells) activated and cultured in GAM bouillon (manufactured by Nissui Pharmaceutical Co., Ltd.) was washed with physiological saline, and then the number of propionic acid bacteria was adjusted to $5 \times 10^9$ cfu/mL to prepare a propionic acid bacterium. This bacterial solution was forcibly administered orally at a dose of 0.2 mL once daily every day from the start date to the end date of the test. To the groups not administered with the propionic acid bacterium (normal diet group, control group and FOS-administered group), physiological saline was forcibly administered orally at a dose of 0.2 mL once daily every day from the start date to the end date of the test. The body weight during the test period, the fat weight around the testes at the time of dissection, and the propionic acid concentration in feces collected at the end day of the test were measured, and the amount of weight gain was calculated from the body weights at the start and end of the test, and used for evaluation.

The propionic acid concentration in the feces was measured by HPLC after extracting the propionic acid from the feces. Specifically, the cryopreserved feces were suspended in PBS, and crotonic acid was added as an internal standard. After centrifugation of the suspension, an equal amount of chloroform was added to the supernatant, the mixture was stirred, and then centrifuged again. The supernatant was collected, frozen and thawed, and centrifuged. Finally, the supernatant was filtered and used in measurement by HPLC. The measurement conditions of HPLC are described below.

Measurement Condition

Mobile phase: 7.5 mM p-toluenesulfonic acid
Reaction solution: 7.5 mM p-toluenesulfonic acid+150 µM EDTA. 2NA+30 mM Bis Tris
Column: column for organic acid analysis, ICSep ICE ORH-801 6.5 mm I.D.×300 mm manufactured by Transgenomic (Tokyo Chemical Industry Co., Ltd.)→two columns connected
Guard column: ICSep ICE ORH-801 4.0 mm I.D.×20 mm
Oven temperature: 55° C.
Flow rate: 0.5 ml/min
Detector: electric conductivity detector CDD-10A (manufactured by Shimadzu Corporation)
Injection volume: 10µ

(2) Test Results

Figure 2:
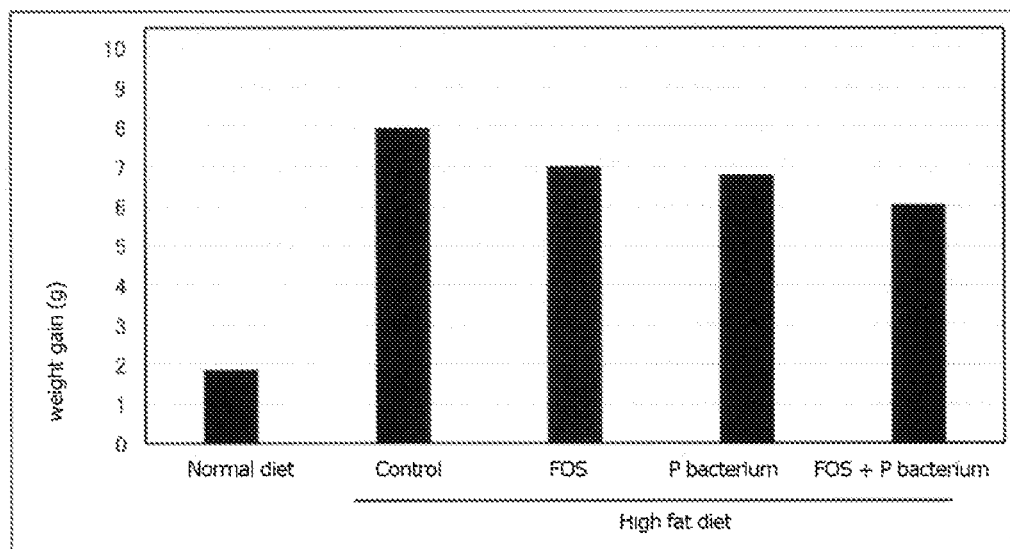
FIG. 2 shows amounts (g) of weight gain of mice at the end day of the test relative to the initial body weights, when normal diet, control, fructo-oligosaccharide (FOS), propionic acid bacterium (P bacterium), and FOS and propionic acid bacterium (FOS+P bacterium) were each fed to mice.

From comparison between the normal diet-administered group and the four high fat diet-administered groups, a clear weight gain was confirmed in the four high fat diet-administered groups (see FIG. 1). In the four high fat diet-administered groups, the body weights from the 6th week on were lower in the propionic acid bacterium-administered group than those in the control group. The group administered with both FOS and propionic acid bacterium showed the lowest values among these groups. In addition, although the amount of weight gain was also low in the FOS-administered group and the propionic acid bacterium-administered group, the group administered with both FOS and propionic acid bacterium (FOS+P bacterium) showed the largest difference in amount of weight gain from the control group. Therefore, it was found that the weight gain is suppressed by simultaneous taking FOS and propionic acid bacterium (see FIG. 2).

Figure 3:
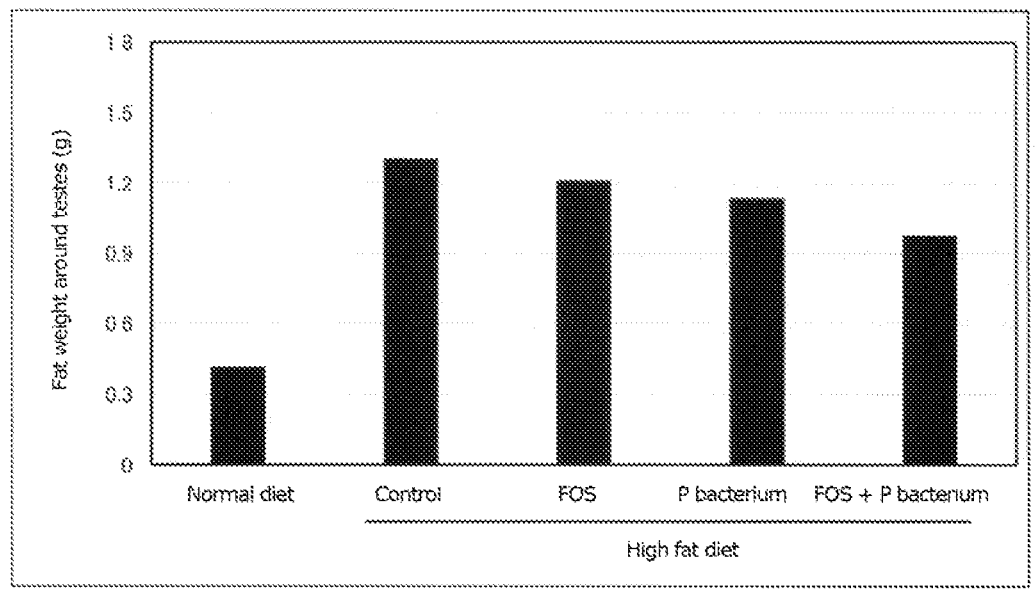
FIG. 3 shows fat weights (g) around the testes of mice at the end day of the test, when normal diet, control, fructo-oligosaccharide (FOS), propionic acid bacterium (P bacterium), and FOS and propionic acid bacterium (FOS+P bacterium) were each fed to mice.

Although the fat weight around the testes was low in the FOS-administered group and the propionic acid bacterium-administered group, as is the case with the body weight, the group administered with FOS and propionic acid bacterium showed the largest difference in fat weight around the testes from the control group. Therefore, it was found that the increase in body fat is suppressed by simultaneous taking FOS and propionic acid bacterium (see FIG. 3).

Figure 4:
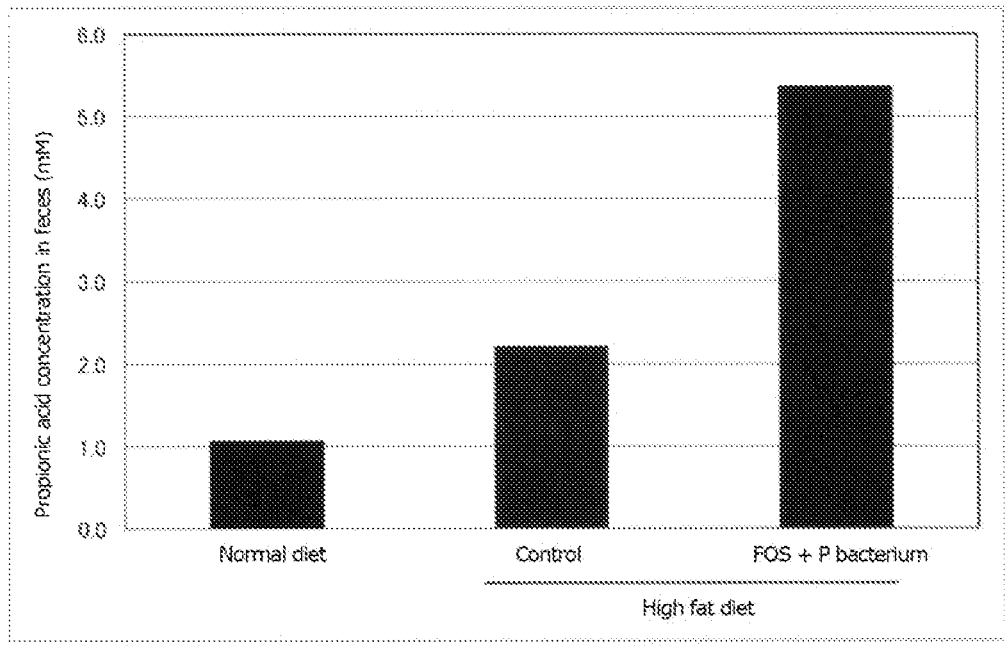
FIG. 4 shows propionic acid concentrations (mM) in feces of mice at the end day of the test, when normal diet, control, and FOS and propionic acid bacterium (FOS+P bacterium) were each fed to mice.

The propionic acid concentration (mM) in the feces was significantly higher in the group administered with both FOS and propionic acid bacterium than that in the control group ($P<0.05$, statistical analysis was performed by paired t-test) (see FIG. 4). In addition, in the group administered with FOS or propionic acid bacterium alone, the value was lower than that in the group administered with both FOS and propionic acid bacterium, but was clearly higher than that in the control group (data not shown). This revealed that taking both FOS and propionic acid bacterium, or taking FOS or propionic acid bacterium alone promotes propionic acid production in the intestine, and, in particular, that taking both FOS and propionic acid bacterium further promotes propionic acid production in the intestine.

The invention claimed is:

1. A method for promoting propionic acid production in a human subject, comprising having the human subject in need thereof ingest an effective amount of a composition comprising a propionic acid bacterium and a fructo-oligosaccharide,
   wherein a content of the fructo-oligosaccharide in the composition is 2 to 8% by mass, and
   wherein the propionic acid bacterium is *Propionibacterium freudenreichii* ET-3 (FERM BP-8115).
2. The method according to claim 1, wherein the composition is a food composition or a pharmaceutical composition.
3. The method according to claim 1, wherein the content of the fructo-oligosaccharide in the composition is 4 to 6% by mass.
4. The method according to claim 1, wherein a content of the propionic acid bacterium in the composition is $1 \times 10^6$ to $1 \times 10^{12}$ cfu/mL.

5. The method according to claim 1, wherein a content of the propionic acid bacterium in the composition is $5\times10^8$ to $5\times10^9$ cfu/mL.

6. The method according to claim 1, wherein the human subject is one in need of suppressing weight gain or in need of reducing body weight.

7. A method for promoting propionic acid production in the intestine in a human subject, comprising having the human subject in need thereof ingest an effective amount of a composition comprising a propionic acid bacterium and a fructo-oligosaccharide,
wherein a content of the fructo-oligosaccharide in the composition is 2 to 8% by mass, and
wherein the propionic acid bacterium is *Propionibacterium freudenreichii* ET-3 (FERM BP-8115).

8. The method according to claim 7, wherein the composition is a food composition or a pharmaceutical composition.

9. The method according to claim 7, wherein the content of the fructo-oligosaccharide in the composition is 4 to 6% by mass.

10. The method according to claim 7, wherein a content of the propionic acid bacterium in the composition is $1\times10^6$ to $1\times10^{12}$ cfu/mL.

11. The method according to claim 7, wherein a content of the propionic acid bacterium in the composition is $5\times10^8$ to $5\times10^9$ cfu/mL.

12. The method according to claim 7, wherein the human subject is one in need of suppressing weight gain or in need of reducing body weight.

* * * * *